United States Patent [19]

Drent

[11] Patent Number: 4,831,187
[45] Date of Patent: May 16, 1989

[54] PROCESS FOR THE PREPARATION OF ESTERS OF ALPHA-ETHYLENICALLY UNSATURATED ALCOHOLS AND ALPHA-ETHYLENICALLY UNSATURATED CARBOXYLIC ACIDS

[75] Inventor: Eit Drent, Amsterdam, Netherlands

[73] Assignee: Shell Oil Company, Houston, Tex.

[21] Appl. No.: 92,004

[22] Filed: Sep. 2, 1986

Related U.S. Application Data

[63] Continuation of Ser. No. 899,137, Aug. 22, 1986, abandoned.

[30] Foreign Application Priority Data

Sep. 27, 1985 [GB] United Kingdom .................. 8523857

[51] Int. Cl.$^4$ ............................................. C07C 67/36
[52] U.S. Cl. ..................................................... 560/207
[58] Field of Search ......................................... 560/207

[56] References Cited

U.S. PATENT DOCUMENTS

| | | | |
|---|---|---|---|
| 3,859,319 | 1/1975 | Mrowca | 560/207 |
| 3,904,672 | 9/1975 | Knifton | 560/207 |
| 4,055,721 | 10/1977 | Kawata et al. | 560/207 |
| 4,480,121 | 10/1984 | Klun et al. | 560/207 |

FOREIGN PATENT DOCUMENTS 2058074A 4/1981 United Kingdom .

*Primary Examiner*—Werren B. Lone

[57] ABSTRACT

A process for preparing esters of alpha-ethylenically unsaturated alcohols and alpha-ethylenically unsaturated carboxylic acids by reacting an acetylenically unsaturated compound with CO and a ketone containing a group HC—C(=O), using a Pd(II) catalyst, a triphenylphosphine in which the phenyl groups carry an electron-withdrawing substituent and a non-carboxylic protonic acid having a $pK_a$ not greater than 1.5.

12 Claims, No Drawings

PROCESS FOR THE PREPARATION OF ESTERS OF ALPHA-ETHYLENICALLY UNSATURATED ALCOHOLS AND ALPHA-ETHYLENICALLY UNSATURATED CARBOXYLIC ACIDS

This is a continuation of application Ser. No. 899,137 filed Aug. 22, 1986, now abandoned.

FIELD OF THE INVENTION

The invention relates to a process for the preparation of esters of alpha-ethylenically unsaturated alcohols and alpha-ethylenically unsaturated carboxylic acids.

BACKGROUND OF THE INVENTION

The esters of alpha-ethylenically unsaturated alcohols and alpha-ethylenically unsaturated carboxylic acids may be used as a starting material for the preparation of polymers. It has now been found that such esters can be prepared with high selectivity and in an acceptable yield using relatively simple starting compounds.

SUMMARY OF THE INVENTION

The invention provides a process for the preparation of esters of alpha-ethylenically unsaturated alcohols and alpha-ethylenically unsaturated carboxylic acids, which process comprises reacting an acetylenically unsaturated compound with carbon monoxide and an enolizable ketone in the presence of a catalytic system formed by combining:
(a) a palladium catalyst,
(b) a phosphine having the general formula I

in which $R^1$, $R^2$ and $R^3$ each individually represent a phenyl group carrying an electron-withdrawing substituent, and
(c) a non-carboxylic protonic acid having a $pK_a$ not greater than 1.5 (measured at 18° C. in aqueous solution).

DESCRIPTION OF THE PREFERRED EMBODIMENTS

The reaction may schematically be represented by means of the following equation:

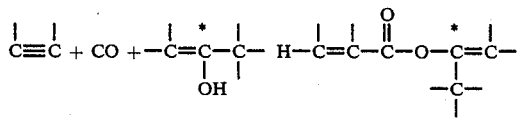

in which the hydroxy compound represents the enolized form of a ketone having the structure;

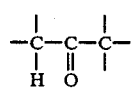

The carbon atoms marked with an asterisk are the same carbon atoms.

The acetylenically unsaturated compound is preferably an optionally substituted alkyne having in the range of from 2 to 30 carbon atoms and in parcitular 2 to 10 carbon atoms per molecule, and preferably 1 to 3 carbon-carbon triple bonds per molecule. Very good results have been obtained with propyne. The acetylenically unsaturated compound may be substituted, for instance with one or more halogen atoms, or cyano, ester, alkoxy or aryl groups. Examples of suitable acetylenically unsaturated compounds are ethyne, 1-butyne, 2-butyne, 1-pentyne, 1-hexyne, 1-heptyne, 1-octyne, 1-nonyne, 1-decyne, benzylethyne and cyclohexylethyne.

The enolizable ketone should have a hydrogen atom bound to a carbon atom adjacent to the carbonyl group. A wide variety of enolizable ketones may be used. The enolizable ketone may have optionally substituted alkyl, optionally substituted cycloalkyl or optionally substituted aryl groups bound to the carbonyl group. Preference is given to alkanones, which have two optionally substituted alkyl groups being bound to the carbonyl group. The optionally substituted alkanones suitably have in the range of from 3 to 30 carbon atoms per molecule. Particularly preferred are methyl alkyl ketones having in the range of from 3 to 30 carbon atoms per molecule. Methyl alkyl ketones having 3 to 4 carbon atoms per molecule, such as acetone and methyl ethyl ketone, are preferred. Enolizable alkyl phenyl ketones such as acetophenone may also be used. Other examples of suitable enolizable ketones are methyl butyl ketone, methyl isobutyl ketone, diheptyl ketone, dioctyl ketone, 3-butylheptyl ethyl ketone, methyl cyclohexyl ketone and ethyl phenyl ketone.

Enolizable ketones which are symmetric with respect to the carbonyl group yield one ester of an alpha-ethylenically unsaturated alcohol and an alpha-ethylenically unsaturated carboxylic acid. Enolizable ketones which are not symmetric with respect to the carbonyl group and in which ketones the two carbon atoms bound to the carbonyl group each carry a hydrogen atom yield two different esters of the same alpha-ethylenically unsaturated carboxylic acid with two different enolized forms being possible.

Both homogeneous and heterogeneous palladium catalysts may be used in the process according to the invention. Homogeneous catalysts are preferred. The palladium catalyst preferably contains a compound of divalent palladium. Suitable homogeneous catalysts are the salts of palladium with, for example, nitric acid, sulfuric acid or, particularly, alkanoic acids. The alkanoic acids having not more than 12 carbon atoms per molecule are preferred. Very good results have been obtained with palladium acetate. Moreover, palladium complexes may be used, for example palladium acetylacetonate, tetrakistriphenylphosphinepalladium, bis-triotolylphosphinepalladium acetate or bistriphenylphosphinepalladium sulfate. Palladium on charcoal and bonded to an ion exchanger, for instance an ion exchanger comprising sulfonic acid groups, is an example of a suitable heterogeneous catalyst.

The three phenyl groups carrying an electron-withdrawing substituent, represented by $R^1$, $R^2$ and $R^3$ in the general formula I may be different but are preferably the same. Preferred electron-withdrawing substituents are halogen atoms, i.e. iodine, bromine, chlorine and fluorine atoms. Very good results have been obtained with tri(p-chlorophenyl)phosphine. Other examples of electron-withdrawing substituents are monochloromethyl, trichloromethyl, trifluoromethyl, nitro and m-methoxy groups. Other examples of phosphines are tri(m-trifluoromethylphenyl)phosphine and tri(m-chlorophenyl)phosphine.

The non-carboxylic protonic acid having a p$K_a$ not greater than 1.5 preferably has a non-coordinating anion, by which is meant that little or no covalent interaction takes place between the palladium and the anion (cf. British Patent Application No. 2,058,074). Typical examples of such anions are $PF_6^-$, $SbF_6^-$, $BF_4^-$ and $ClO_4^-$. Preferred acids are sulfonic acids and acids that can be formed, possibly in situ, by interacting a Lewis acid such as, for example, $BF_3$, $AsF_5$, $SbF_5$, $PF_5$, $TaF_5$ or $NbF_5$ with a Broensted acid such as, for example, a hydrogen halide, in particular HF, or fluorosulfonic acid, orthophosphoric acid or sulfuric acid. Specific examples of acids of the latter type are fluorosilicic acid, $HBF_4$, $HPF_6$ and $HSbF_6$. Examples of suitable sulfonic acids are fluorosulfonic acid and chlorosulfonic acid and the hereinafter specified sulfonic acids.

A preferred group of non-carboxylic protonic acids having a p$K_a$ not greater than 1.5 are those having the general formula II

(II)

wherein Z represents sulfur or chlorine and, if Z is chlorine, $R^4$ represents oxygen and, if Z is sulfur, $R^4$ represents an OH group or an optionally substituted hydrocarbon group.

When the acids of the general formula II are used in the process according to the invention, the anions thereof can be considered to be non-coordinating.

The optionally substituted hydrocarbon group represented by $R^4$ is preferably an alkyl, aryl, aralkyl or alkaryl group having 1 to 30, in particular 1 to 14, carbon atoms. The hydrocarbon group may be substituted, for example, with halogen atoms, in particular fluorine atoms. Examples of suitable acids of the general formula II are perchloric acid, sulfuric acid, 2-hydroxypropane-2-sulfonic acid, benzenesulfonic acid, 1-naphthalenesulfonic acid, 2-naphthalenesulfonic acid, p-toluenesulfonic and trifluoromethanesulfuric acid, p-toluenesulfonic acid being the most preferred.

The quantity of the compound of divalent palladium to be used in the process according to the invention is not critical and may vary within wide limits. Preference is given to the use of quantities in the range between $10^{-5}$ and $10^{-1}$ gram atom palladium per mol of compound of the general formula II.

The molar ratio of organic phosphine to palladium is not critical and may vary within wide limits. If less than 5 mol of the organic phosphine are used per gram atom of palladium, selectivity to compounds of the general formula I is still very high, but the reaction rate is moderate. Very high selectivities and very high reaction rates are obtained when more than 5 mol and in particular more than 20 mol of the phosphine having the general formula I are used per gram atom of palladium. In general, more than 500 mol of phosphine per gram atom of palladium need not be used.

The number of equivalents of the phosphine having the general formula I which is used per equivalent of non-carboxylic protonic acid having a p$K_a$ not greater than 1.5 is not critical and may vary within wide limits. This number of equivalents is suitably in the range of from 0.5 to 50. A side reaction which may occur is the reaction of 2 mol of the acetylenically unsaturated compound with CO with formation of the acetylenically and ethylenically unsaturated ketones, which is subject matter of Applicant's British Patent Application No. 8,523,858 filed on even date herewith. This side reaction is considerably reduced when the said member of equivalents of the phosphine is higher than 1.0. Said number is suitably in the range of from 1.0 to 20.

A separate solvent is not essential in the process according to the invention, and often a large excess of one of the reactants, usually the ketone may form a convenient liquid phase. However, it may in some cases be desirable to use a separate solvent and any inert solvent may be used. A suitable solvent may, for example, be selected from aromatic hydrocarbons, for example benzene, toluene, ethylbenzene and the three xylenes; sulfoxides, for example dimethyl sulfoxide and diethyl sulfoxide; sulfones, for example diisopropyl sulfone and tetrahydrothiophene 1,1-dioxide (also referred to as "sulfolane") and ethers, for example anisole, 2,5,8-trioxanonane (also referred to as "diglyme"), diphenyl ether and diisopropyl ether.

In the process according to the invention, the carbon monoxide may be used pure or diluted with an inert gas, such as nitrogen, noble gases or carbon dioxide. Generally, the presence of more than 10% by volume of hydrogen is undesirable, since under the reaction conditions it may cause hydrogenation of carbon-carbon double or triple bonds. Preference is given to the use of pure carbon monoxide or a carbon monoxide-containing gas which contains less than 5% by volume of hydrogen.

The process according to the invention permits the use of very mild reaction conditions. Temperatures in the range of from 50° C. to 200° C., especially 100° C. to 150° C., are generally suitable. The pressure may vary over a wide range. Generally, a pressure in the range of from 1 to 100 bar is suitable, with pressures of from 5 to 50 bar being preferred. Pressures higher than 100 bar may be used, but are usually economically unattractive.

The process according to the invention may be carried out batchwise, continuously or semi-continuously.

The invention is further described by means of the following examples which are intended for illustration and are not to be construed as limiting the invention. The selectivity to a certain compound, expressed in a percentage, is defined as 100 a/b, in which "a" is the amount of ketone that has been converted into that certain compound "b" is the total amount of that ketone that has been converted.

EXAMPLE 1

A 250-ml magnetically stirred Hastelloy C autoclave ("Hastelloy" is a trade name) was charged with toluene (50 ml), acetone (20 ml), palladium acetate (0.2 mmol), tri(p-chlorophenyl)phosphine (10 mmol) and p-toluenesulfonic acid (10 mmol). The autoclave was flushed with carbon monoxide, filled with carbon monoxide and propyne until partial pressures thereof of 20 and 2 bar, respectively, were obtained and heated to a temperature of 115° C. After a reaction time of 5 h at this temperature the contents of the autoclave were analyzed by means of gas-liquid chromatography. The conversion of acetone was 30% and the selectivity to isopropenyl methacrylate 60%; the selectivity to 2-methyl-1-hexene-3-one-4-yne (formed by reaction of 2 mol of propyne with 1 mol of carbon monoxide) was 40%.

EXAMPLE 2

The procedure of Example 1 was repeated with the difference that only 8 mmol of p-toluenesulfonic acid was used. The same results were obtained.

EXAMPLE 3

The procedure of Example 1 was repeated with the difference that 30 mmol instead of 10 mmol of tri(p-chlorophenyl)phosphine was used. The conversion of acetone was 30% with a selectivity to isopropenyl methacrylate of 90%.

EXAMPLE 4

The procedure of Example 3 was repeated with the difference that 20 ml of acetophenone instead of 20 ml of acetone was used. The conversion of acetophenone was 10% with a selectivity to 1-phenylvinyl methacrylate of 92%. The compound 1-phenylvinyl methacrylate is believed to be novel.

COMPARATIVE EXPERIMENT A

The procedure of Example 1 was repeated with the difference that the tri(p-chlorophenyl)phosphine (10 mmol) was replaced with triphenylphosphine (10 mmol) and that methacrylic acid (1 ml) as also present. The conversion of acetone was 30% after a reaction time of 5 h, with a selectivity to isopropenyl methacrylate of less than 5%. Comparison of this result with that of Example 1 shows that the phenyl groups in the phosphine should carry an electron-withdrawing substituent.

COMPARATIVE EXPERIMENT B

The procedure of Example 1 was repeated with the difference that p-toluenesulfonic acid (10 mmol) was replaced with methacrylic acid (20 mmol). The conversion of acetone was below 5%.

COMPARATIVE EXPERIMENT C

The procedure of Example 1 was repeated with the difference that p-toluenesulfonic acid (10 mmol) was replaced with orthophosphoric acid ($pK_a = 2.2$, 10 mmol). The conversion of acetone was below 5%.

I claim:

1. A process for the preparation of esters of alpha-ethylenically unsaturated alcohols and alpha-ethylenically unsaturated carboxylic acids, which process comprises reacting an alkyne having in the range of from 2 to 10 carbon atoms per molecule with carbon monoxide and an enolizable alkanone having in the range of from 3 to 30 carbon atoms per molecule in the presence of a catalytic system formed by combining:
   (a) a palladium catalyst,
   (b) a phosphine having the general formula I

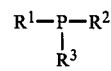

in which $R^1$, $R^2$ and $R^3$ each individually represent a phenyl group carrying an electron-withdrawing substituent selected from the group consisting of iodine, bromine, chlorine and fluorine atoms, and
   (c) a non-carboxylic protonic acid having a $pK_a$ not greater than 1.5 (measured at 18° C. in aqueous solution).

2. The process of claim 1 wherein the alkyne is propyne.

3. The process of claim 1 wherein the alkanone is a methyl alkyl ketone.

4. The process of claim 3 wherein the alkanone has 3 to 4 carbon atoms per molecule.

5. The process of claim 1 wherein the palladium catalyst contains a compound of divalent palladium.

6. The process of claim 5 wherein the compound of divalent palladium is a palladium alkanoate.

7. The process of claim 6 wherein the palladium alkanoate is palladium acetate.

8. The process of claim 1 wherein the phosphine of the general formula I is tri(p-chlorophenyl)phosphine.

9. The process of claim 1 wherein the protonic acid has the general formula II

in which Z represents a sulfur or a chlorine atoms, and, if Z represents a chlorine atom, $R^4$ represents an oxygen atoms, and, if Z represents a sulfur atom, $R^4$ represents an OH group or a hydrocarbon group.

10. The process of claim 9 wherein the hydrocarbon group represented by $R^4$ is an alkyl, aryl or aralkyl group having not more than 30 carbon atoms.

11. The process of claim 10 wherein the acid is p-toluenesulfonic acid.

12. The process of claim 1 wherein the said process is carried out at a temperature in the range of from 50° C. to 200° C.

* * * * *